(12) United States Patent
Speziali

(10) Patent No.: US 10,582,924 B2
(45) Date of Patent: Mar. 10, 2020

(54) THORASCOPIC HEART VALVE REPAIR METHOD

(71) Applicant: Mayo Foundation For Medical Education and Research, Rochester, MN (US)

(72) Inventor: Giovanni Speziali, Pittsburgh, PA (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 200 days.

(21) Appl. No.: 15/634,412

(22) Filed: Jun. 27, 2017

(65) Prior Publication Data

US 2017/0290582 A1 Oct. 12, 2017

Related U.S. Application Data

(60) Continuation of application No. 14/614,570, filed on Feb. 5, 2015, now Pat. No. 9,700,300, which is a
(Continued)

(51) Int. Cl.
*A61B 17/04* (2006.01)
*A61B 17/062* (2006.01)
(Continued)

(52) U.S. Cl.
CPC ............ *A61B 17/0469* (2013.01); *A61B 1/07* (2013.01); *A61B 5/0084* (2013.01); *A61B 5/02028* (2013.01); *A61B 5/4836* (2013.01); *A61B 17/0482* (2013.01); *A61B 17/0483* (2013.01); *A61B 17/0491* (2013.01); *A61B 17/06* (2013.01); *A61B 17/0625* (2013.01);
(Continued)

(58) Field of Classification Search
CPC ............ A61B 17/0469; A61B 17/0482; A61B 17/0483; A61B 17/04; A61B 2017/00243; A61B 2017/00238; A61B 2017/0475; A61B 2017/0472; A61B 2017/00783; A61F 2/2427
See application file for complete search history.

(56) References Cited

U.S. PATENT DOCUMENTS 2,751,908 A   6/1956   Wallace
3,664,330 A   5/1972   Deutsch
(Continued)

FOREIGN PATENT DOCUMENTS

JP   H04307052 A   10/1992
JP   H06142114 A   5/1994
(Continued)

OTHER PUBLICATIONS

US 6,197,052 B1, 03/2001, Cosgrove et al. (withdrawn)
(Continued)

*Primary Examiner* — Christopher L Templeton
(74) *Attorney, Agent, or Firm* — Quarles & Brady LLP

(57) ABSTRACT

A method for performing thorascopic repair of heart valves includes inserting an instrument through the chest cavity and into a heart chamber providing access to a valve needing repair. A movable tip on the shaft is operable to capture a valve leaflet and a needle is operable to penetrate a captured valve leaflet and draw a suture therethrough.

19 Claims, 10 Drawing Sheets

Related U.S. Application Data continuation of application No. 12/709,220, filed on Feb. 19, 2010, now Pat. No. 8,968,338, which is a division of application No. 11/813,695, filed as application No. PCT/US2006/001699 on Jan. 19, 2006, now Pat. No. 8,465,500.

(60) Provisional application No. 60/645,677, filed on Jan. 21, 2005.

(51) Int. Cl.
| | |
|---|---|
| A61B 1/07 | (2006.01) |
| A61B 5/00 | (2006.01) |
| A61B 5/02 | (2006.01) |
| A61B 17/29 | (2006.01) |
| A61B 17/06 | (2006.01) |
| A61B 1/00 | (2006.01) |
| G02B 23/24 | (2006.01) |
| A61B 90/30 | (2016.01) |
| A61B 17/295 | (2006.01) |
| A61B 17/00 | (2006.01) |

(52) U.S. Cl.
CPC .......... *A61B 17/29* (2013.01); *A61B 1/00167* (2013.01); *A61B 17/295* (2013.01); *A61B 2017/00057* (2013.01); *A61B 2017/00243* (2013.01); *A61B 2017/00783* (2013.01); *A61B 2017/0608* (2013.01); *A61B 2090/306* (2016.02); *G02B 23/2469* (2013.01)

(56) References Cited

U.S. PATENT DOCUMENTS

| | | |
|---|---|---|
| 3,667,474 A | 6/1972 | Lapkin et al. |
| 3,842,840 A | 10/1974 | Schweizer |
| 4,258,716 A | 3/1981 | Sutherland |
| 4,351,345 A | 9/1982 | Carney |
| 4,759,348 A | 7/1988 | Cawood |
| 4,935,027 A | 6/1990 | Yoon |
| 4,957,498 A | 9/1990 | Caspari et al. |
| 4,967,498 A | 9/1990 | Caspari |
| 4,960,424 A | 10/1990 | Grooters |
| 4,972,874 A | 11/1990 | Jackson |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth |
| 5,336,229 A | 8/1994 | Noda |
| 5,383,877 A | 1/1995 | Clarke |
| 5,431,666 A | 7/1995 | Sauer et al. |
| 5,452,733 A | 9/1995 | Sterman et al. |
| 5,474,519 A | 12/1995 | Bloomer |
| 5,547,455 A | 8/1996 | McKenna et al. |
| 5,571,215 A | 11/1996 | Sterman et al. |
| 5,601,578 A | 2/1997 | Murphy |
| 5,626,607 A | 5/1997 | Malecki |
| 5,653,716 A | 8/1997 | Malo et al. |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,762,458 A | 6/1998 | Wang et al. |
| 5,762,613 A | 6/1998 | Sutton et al. |
| 5,769,791 A | 6/1998 | Benaron et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,857,961 A | 1/1999 | Vanden Hoek et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr. et al. |
| 5,972,004 A | 10/1999 | Williamson et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr. et al. |
| 6,050,936 A | 4/2000 | Schweich, Jr. et al. |
| 6,053,933 A | 4/2000 | Balazs et al. |
| 6,059,715 A | 5/2000 | Schweich, Jr. et al. |
| 6,077,214 A | 6/2000 | Mortier et al. |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr. et al. |
| 6,162,233 A | 12/2000 | Williamson |
| 6,165,119 A | 12/2000 | Schweich, Jr. et al. |
| 6,165,120 A | 12/2000 | Schweich, Jr. et al. |
| 6,165,183 A | 12/2000 | Kuehn et al. |
| 6,178,346 B1 | 1/2001 | Amundson et al. |
| 6,183,411 B1 | 2/2001 | Mortier et al. |
| 6,190,357 B1 | 2/2001 | Ferrari et al. |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,270,508 B1 | 8/2001 | Klieman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund |
| 6,619,291 B2 | 9/2003 | Hlavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,629,984 B1 | 10/2003 | Chan |
| 6,645,205 B2 | 11/2003 | Ginn |
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,770,083 B2 | 3/2004 | Seguin |

(56) References Cited

U.S. PATENT DOCUMENTS

| | | |
|---|---|---|
| 6,718,985 B2 | 4/2004 | Hlavka et al. |
| 6,723,038 B1 | 4/2004 | Schroeder et al. |
| 6,733,509 B2 | 5/2004 | Nobles et al. |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,084 B1 | 8/2004 | Bain et al. |
| 6,793,618 B2 | 9/2004 | Schweich, Jr. et al. |
| 6,802,860 B2 | 10/2004 | Dosgrove et al. |
| 6,808,488 B2 | 10/2004 | Mortier et al. |
| 6,810,882 B2 | 11/2004 | Langbert et al. |
| 6,840,246 B2 | 1/2005 | Downing |
| 6,858,003 B2 | 2/2005 | Evans et al. |
| 6,875,224 B2 | 5/2005 | Grimes |
| 6,893,448 B2 | 5/2005 | O'Quinn et al. |
| 6,896,686 B2 * | 5/2005 | Weber ............... A61B 17/0469 606/139 |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Sequin |
| 7,294,148 B2 | 11/2007 | McCarthy et al. |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,465,500 B2 | 6/2013 | Speziali |
| 8,968,338 B2 | 3/2015 | Speziali |
| 9,364,213 B2 | 6/2016 | Speziali |
| 9,700,300 B2 | 7/2017 | Speziali |
| 2001/0005787 A1 | 6/2001 | Oz et al. |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0029080 A1 | 3/2002 | Mortier et al. |
| 2002/0049402 A1 | 4/2002 | Peacock, III et al. |
| 2002/0077524 A1 | 6/2002 | Schweich, Jr. et al. |
| 2002/0169359 A1 | 11/2002 | McCarthy et al. |
| 2002/0173694 A1 | 11/2002 | Mortier et al. |
| 2002/0183766 A1 | 12/2002 | Sequin |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano et al. |
| 2003/0078599 A1 * | 4/2003 | O'Quinn ............ A61B 17/0469 606/144 |
| 2003/0078600 A1 | 4/2003 | O'Quinn et al. |
| 2003/0105519 A1 | 6/2003 | Fasol et al. |
| 2003/0120341 A1 | 6/2003 | Shennib et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. et al. |
| 2003/0167071 A1 | 9/2003 | Martin et al. |
| 2003/0171641 A1 | 9/2003 | Schweich, Jr. et al. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama et al. |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0236373 A1 * | 11/2004 | Anspach, III ...... A61B 17/0401 606/232 |
| 2004/0243229 A1 | 12/2004 | Vidlund et al. |
| 2004/0267083 A1 | 12/2004 | McCarthy et al. |
| 2005/0021055 A1 | 1/2005 | Toubia et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. et al. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove et al. |
| 2005/0216039 A1 | 9/2005 | Lederman |
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0127509 A1 | 6/2006 | Eckman et al. |
| 2006/0135993 A1 | 6/2006 | Seguin |
| 2006/0149123 A1 | 7/2006 | Vidlund et al. |
| 2006/0161040 A1 | 7/2006 | McCarthy et al. |

(56) References Cited

U.S. PATENT DOCUMENTS

| | | |
|---|---|---|
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0241340 A1 | 10/2006 | Vidlund et al. |
| 2006/0287657 A1 | 12/2006 | Bachman |
| 2007/0002627 A1 | 1/2007 | Youn |
| 2007/0027451 A1 | 2/2007 | Desinger et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy et al. |
| 2007/0118154 A1 | 5/2007 | Crabtree |
| 2007/0118155 A1 | 5/2007 | Goldfarb et al. |
| 2007/0118213 A1* | 5/2007 | Loulmet ............ A61B 17/0401 623/2.1 |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0027468 A1 | 1/2008 | Fenton |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold et al. |
| 2008/0091264 A1 | 4/2008 | Machold et al. |
| 2008/0097482 A1 | 4/2008 | Bain et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2008/0188873 A1 | 8/2008 | Speziali |
| 2008/0195200 A1 | 8/2008 | Vidlund et al. |
| 2008/0208006 A1 | 8/2008 | Farr |
| 2008/0228223 A1 | 9/2008 | Alkhatib |
| 2009/0105729 A1 | 4/2009 | Zentgraf |
| 2009/0105751 A1 | 4/2009 | Zentgraf |
| 2009/0131880 A1 | 5/2009 | Speziali et al. |
| 2009/0156995 A1 | 6/2009 | Martin et al. |
| 2009/0163934 A1 | 6/2009 | Raschdort, Jr. et al. |
| 2009/0259304 A1 | 10/2009 | O'Beirne et al. |
| 2010/0174297 A1 | 7/2010 | Speziali |

FOREIGN PATENT DOCUMENTS

| | | |
|---|---|---|
| WO | 9900059 A1 | 1/1999 |
| WO | 9930647 A1 | 6/1999 |
| WO | 0006026 A2 | 2/2000 |
| WO | 0006027 A2 | 2/2000 |
| WO | 0006028 A1 | 2/2000 |
| WO | 0016700 A1 | 3/2000 |
| WO | 0166018 A1 | 9/2001 |
| WO | 0195809 A1 | 12/2001 |
| WO | 03001893 A2 | 1/2003 |
| WO | 03059209 A2 | 7/2003 |
| WO | 03079937 A2 | 10/2003 |
| WO | 03082157 A2 | 10/2003 |
| WO | 2004021893 A1 | 3/2004 |
| WO | 2004043265 A2 | 5/2004 |
| WO | 2005039428 A2 | 5/2005 |
| WO | 2005094525 A2 | 10/2005 |
| WO | 2006032051 A2 | 3/2006 |
| WO | 2006065966 A2 | 6/2006 |
| WO | 2006078694 A2 | 7/2006 |
| WO | 2006116310 A2 | 11/2006 |
| WO | 2006127509 A2 | 11/2006 |
| WO | 2007002627 A1 | 1/2007 |
| WO | 2007027451 A2 | 3/2007 |
| WO | 2007062128 A2 | 5/2007 |
| WO | 2007081418 A1 | 7/2007 |
| WO | 2007117612 A1 | 10/2007 |
| WO | 2008010738 A2 | 1/2008 |
| WO | 2009052528 A2 | 4/2009 |

OTHER PUBLICATIONS

PCT International Search Report and Written Opinion, PCT/US06/01699, dated May 6, 2008.

European Patent Office, Supplementary Partial European Search Report, EP 06718728.6, dated Nov. 11, 2009.

Edwards Lifesciences, Port Access System for Mitral Valve Repair Proves Its Value in Study, medGadget—Internet Journal of Emerging Medical Technologies, Jul. 9, 2009.

European Association for Cardio-Thoracic Surgery, Interactive CardioVascular and Thoracic Surgery, Abstracts: Suppl. 3 to vol. 7, Sep. 2008, pp. 205-254.

PCT International Preliminary Report on Patentability, PCT/US2008/080560, dated Apr. 20, 2010.

* cited by examiner

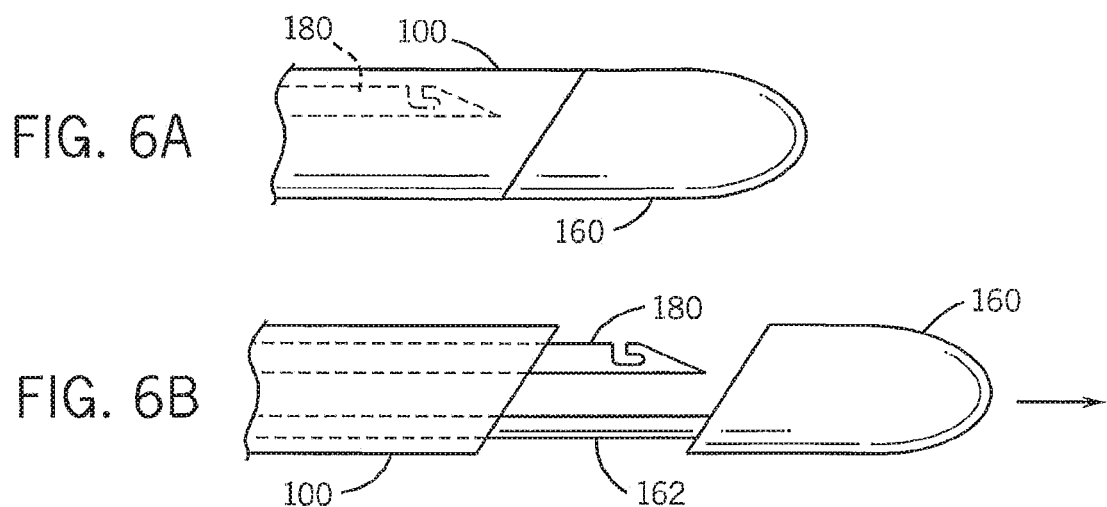
FIG. 6A
FIG. 6B
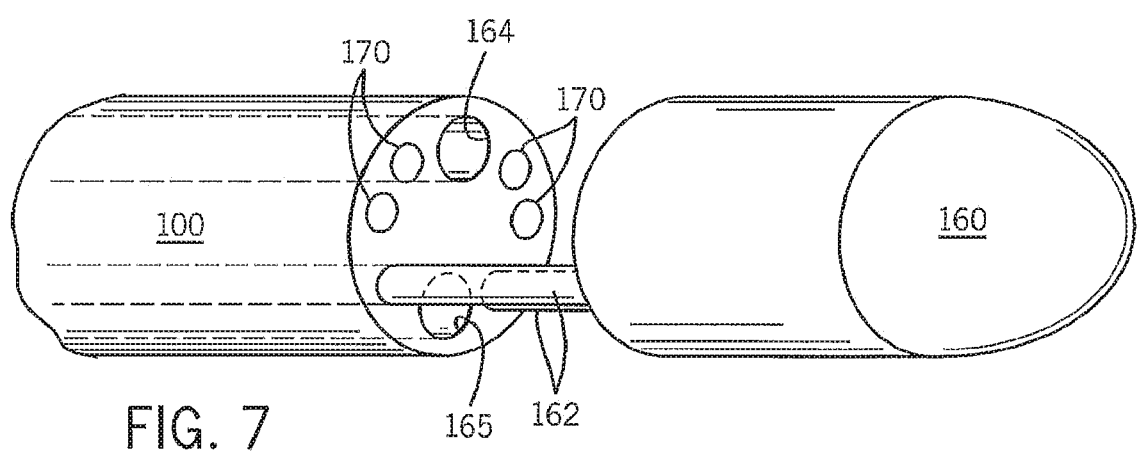
FIG. 7
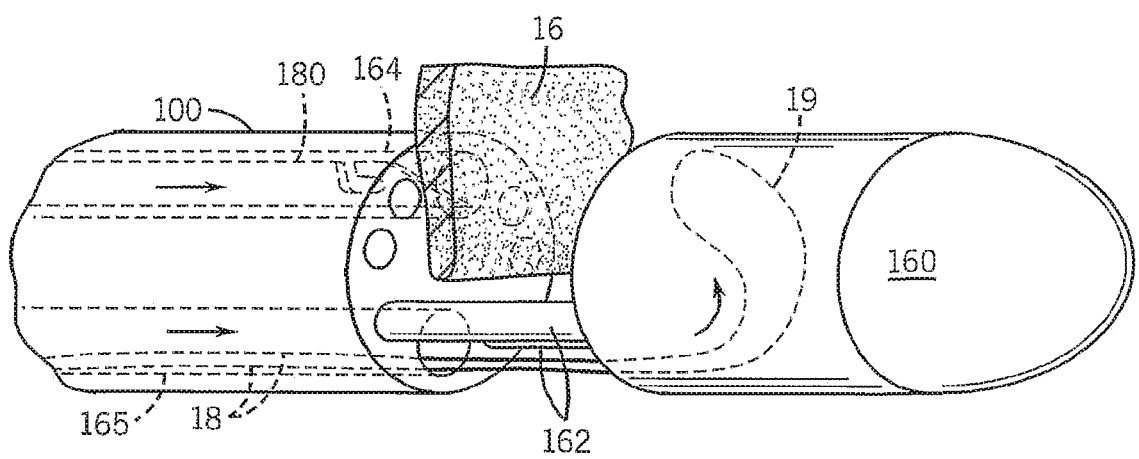
FIG. 8A

THORASCOPIC HEART VALVE REPAIR METHOD

CROSS-REFERENCE TO RELATED APPLICATIONS

This application is a continuation application of U.S. patent application Ser. No. 14/614,570, filed Feb. 5, 2015, which is a continuation application of U.S. patent application Ser. No. 12/709,220 filed Feb. 19, 2010, now U.S. Pat. No. 8,968,338, which is a divisional application of U.S. patent application Ser. No. 11/813,695, filed Jul. 11, 2007, now U.S. Pat. No. 8,465,500, which is a 371 of PCT/US06/01699 filed Jan. 19, 2006, which claims the benefit of U.S. Provisional Patent Application No. 60/645,677 filed Jan. 21, 2005.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electro-physiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts, as described in Bodnar and Frater, Replacement Cardiac Valves 1-357 (1991), which is incorporated herein by reference. A comprehensive discussion of heart valve diseases and the surgical treatment thereof is found in Kirklin and Barratt-Boyes, Cardiac Surgery 323-459 (1986), the complete disclosure of which is incorporated herein by reference.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into a position accessible through the sternotomy. An opening, or atriotomy, is then made in the left atrium, anterior to the right pulmonary veins. The atriotomy is retracted by means of sutures or a retraction device, exposing the mitral valve directly posterior to the atriotomy. One of the fore mentioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

The mitral and tricuspid valves inside the human heart include an orifice (annulus), two (for the mitral) or three (for the tricuspid) leaflets and a subvalvular apparatus. The subvalvular apparatus includes multiple chordae tendinae, which connect the mobile valve leaflets to muscular structures (papillary muscles) inside the ventricles. Rupture or elongation of the chordae tendinae result in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This operation is generally carried out through a median sternotomy and requires cardiopulmonary bypass with aortic cross-clamp and cardioplegic arrest of the heart.

SUMMARY OF THE INVENTION

The present invention is a method and apparatus for performing a minimally invasive thoracoscopic repair of heart valves while the heart is beating. More specifically the method includes inserting an instrument through the subject's chest wall and through the heart wall. The instrument carries on its distal end a movable element which is manipulated to grasp a valve leaflet and hold it while a needle mechanism punctures the valve leaflet and loops a suture around a portion of the valve leaflet. The instrument is withdrawn from the heart along with the suture and the suture is tied off at the apex of the heart after adjusting its tension for optimal valve operation as observed with an ultrasonic imaging system.

In addition to grasping and needle mechanisms, the instrument includes fiber optics which provide direct visual indication that the valve leaflet is properly grasped. A set of illuminating fibers terminate at the distal end of the instrument around the needle mechanism in close proximity to a set of sensor fibers. The sensor fibers convey light from the distal end of the instrument to produce an image for the operator. When a valve leaflet is properly grasped, light from the illuminating fibers is reflected off the leaflet surface back through the sensor fibers. On the other hand, if the valve leaflet is not properly grasped the sensor fibers see blood.

A general object of the invention is to provide an instrument and procedure which enables heart valves to be repaired without the need for open heart surgery. The instrument is inserted through an opening in the chest wall and into a heart chamber while the heart is beating. The instrument enables repair of a heart valve, after which it is withdrawn from the heart and the chest.

BRIEF DESCRIPTION OF THE DRAWINGS

FIG. 6A is a detailed side elevation view of the distal end of an instrument embodying the invention showing the tip in a closed position.

FIG. 6B is a detailed side elevation view of the distal end of an instrument embodying the invention showing rods inside the instrument that are capable of sliding to move the tip to an open position.

FIG. 7 is a detailed isometric view of the distal end of an instrument embodying the invention showing the needle lumen and four fiberoptic channels that are disposed around the needle lumen.

FIG. 8A is a detailed isometric view of the preferred embodiment of the suture deployment system showing the positioning of a heart valve leaflet with respect to the instrument.

DETAILED DESCRIPTION OF THE PREFERRED EMBODIMENT

Figure 1:
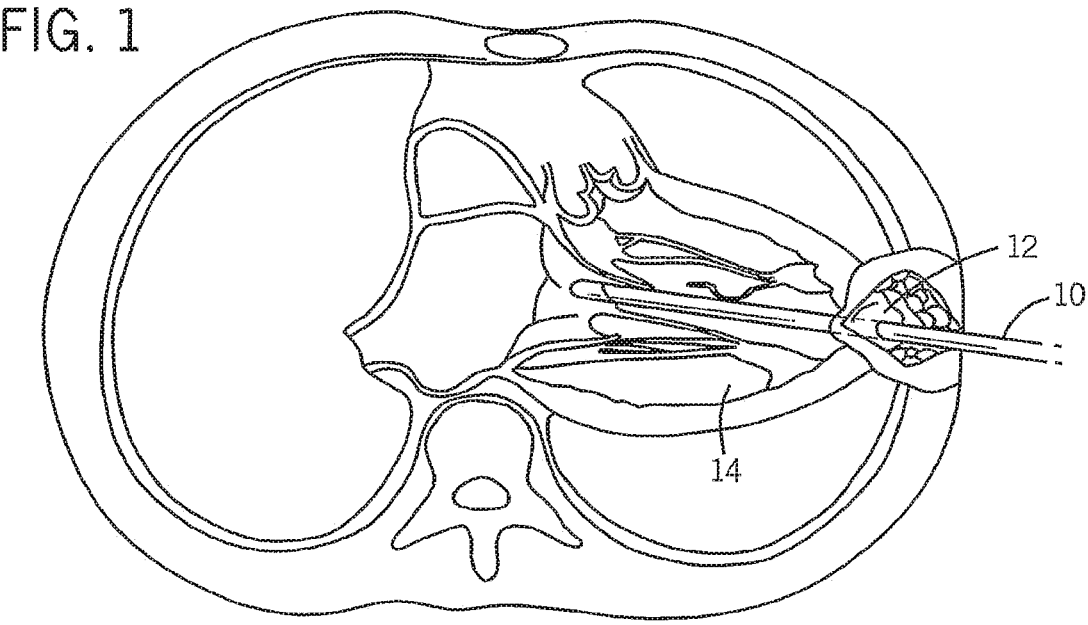
FIG. 1 is a cut-out view of a patient's chest showing an instrument embodying the invention being inserted into a patient's chest cavity through a thorascopic port that is inserted into the patient's chest.

Under general anesthesia and double-lumen ventilation, the patient is prepped and draped so as to allow ample surgical access to the right lateral, anterior and left lateral chest wall (from the posterior axillary line on one side to the posterior axillary line on the other side). As shown in FIG. 1, one or more thoracoscopic ports are inserted in the left chest through the intercostal spaces and an instrument 10 is inserted through one of these ports into the chest cavity. Alternatively, a small (3-5 cm) left thoracotomy is performed in the fifth or sixth intercostals space on the anterior axillary line. The patient is fully heparinized. After collapsing the left lung, the pericardium overlying the apex 12 of the left ventricle 14 is opened and its edges are suspended to the skin incision line. This provides close access to the apex of the heart. Guidance of the intracardiac procedure is provided by a combination of transesophageal or intravascular echocardiography (not shown in the drawings) and with direct visualization through a fiber-optical system built into the instrument 10 as will be described in detail below. A double-pledgeted purse-string suture is placed on the apex of the left ventricle 12 and a stab incision is made at that location. The surgical instrument 10 is inserted through this incision, into the left ventricular chamber 14 of the beating heart.

Figure 2:
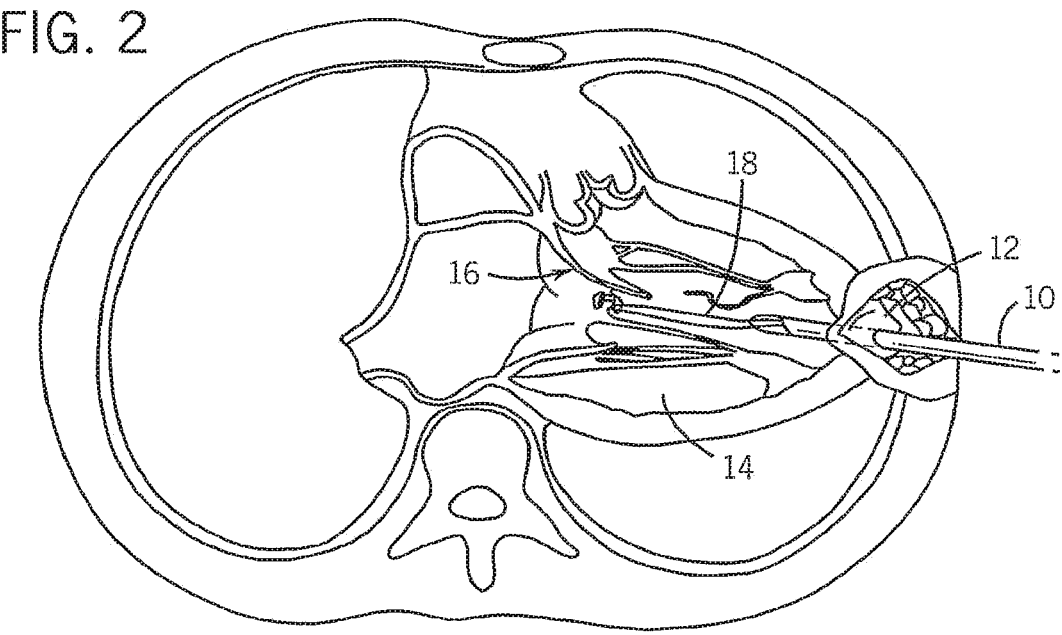
FIG. 2 is a cut-out view of a patient's chest showing an instrument embodying the invention grasping a prolapsing segment of the mitral valve inside the patient's chest cavity and securing an artificial chorda to the free edge of the prolapsing segment of the mitral valve.
Figure 3:
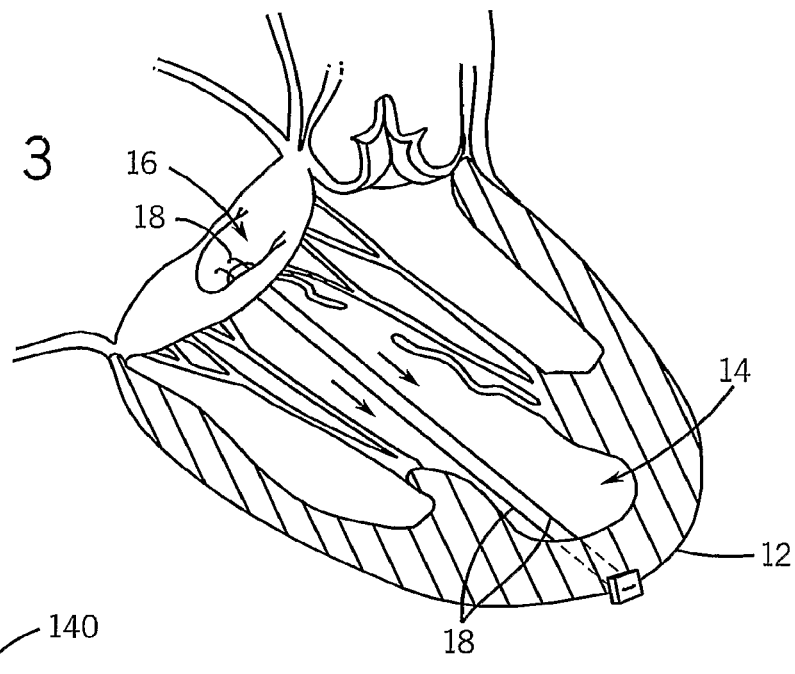
FIG. 3 is a cut-out view of a patient's chest cavity showing an instrument embodying the invention tensioning the neo-implanted chorda.

Referring particularly to FIG. 2, the instrument 10 may be used to grasp a prolapsing segment of the mitral valve 16 and an artificial chorda 18 may be secured to its free edge. Accurate positioning of the implanted artificial chorda 18 is guaranteed by both echo and direct fiberoptic visualization as will be described in detail below. The instrument 10 is then withdrawn from the left ventricle chamber 14 pulling the unattached end of the neo-implanted chorda 18 with it. Hemostasis is achieved by tying the purse-string suture around the incision in the left ventricular apex 12 after the instrument 10 and chorda 18 are withdrawn. As shown in FIG. 3, the neo-implanted chorda 18 is appropriately tensioned under direct echo-Doppler visualization and secured outside the apex 12 of the heart. That is, a tension is placed on the neo-implanted chorda 18 and the operation of the repaired valve 16 is observed on the ultrasound image. The tension is adjusted until regurgitation is minimized.

While a single chorda 18 is implanted in the above description, additional chorda, or sutures, can be implanted and attached to the apex 12 of the heart wall with optimal tension. In this case the tensions in all the neo-implanted chorda 18 are adjusted until optimal valve operation is achieved.

Figure 4:
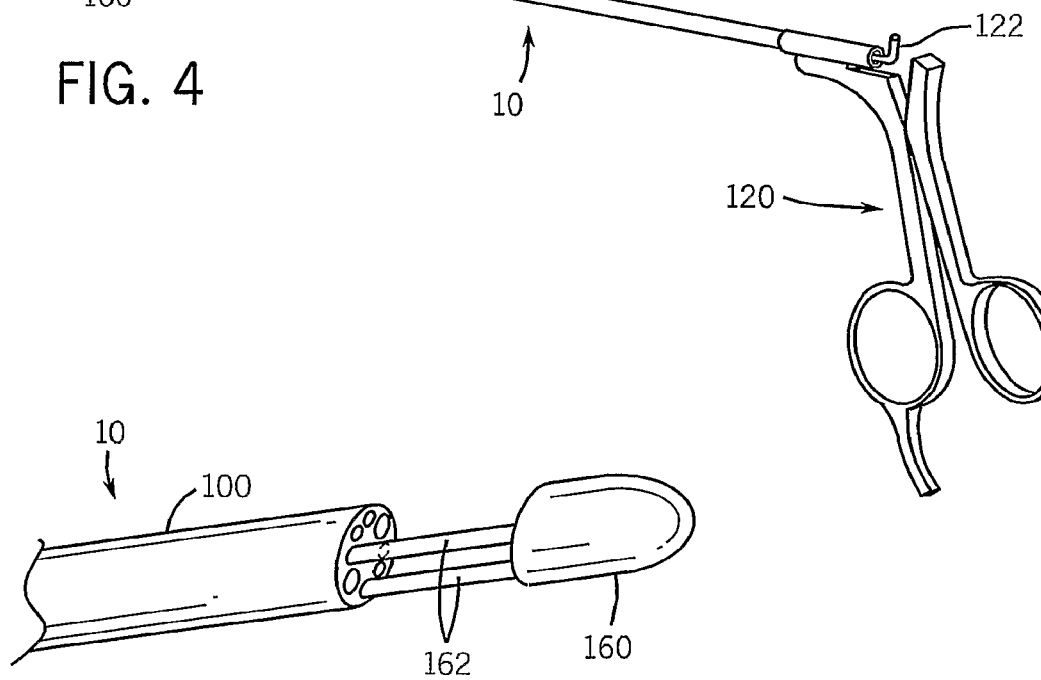
FIG. 4 is an isometric view of an instrument embodying the invention.
Figure 5:
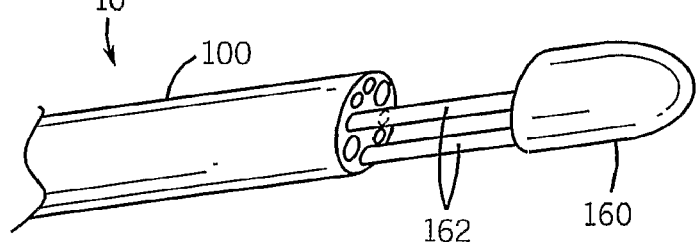
FIG. 5 is a detailed isometric view of the distal end of an instrument embodying the invention.

As shown in FIGS. 4 and 5, the instrument 10 used to perform the above procedure includes a rigid metal shaft 100 having a handle 120 at its extrathoracic (proximal) end which enables the instrument to be manipulated and guided into position. Actuating mechanisms for controlling the grasping mechanism and needle mechanism located at the distal end 140 of the instrument are also mounted near the handle 120. As will be described below, the grasping mechanism is operated by squeezing the scissor-grip handle 120, and the needle mechanism is operated by moving an upturned control shaft 122.

Located on the distal, intracardiac end 140 of the instrument 10 is a grasping mechanism which can be operated to hold a prolapsing valve leaflet. As shown in FIGS. 6 and 7, in the preferred embodiment this mechanism is a tip 160 which is supported on the distal end of the shaft 100 by a set of rods 162. The rods 162 slide within the shaft 100 to move the tip 160 between an open position as shown in FIGS. 6B and 7 and a closed position as shown in FIG. 6A when the scissor-grip handle 120 is operated. As will be explained below, a mitral valve leaflet is located in the gap between the open tip 160 and the distal end of shaft 100 and it is captured by closing the tip 160 to pinch the valve leaflet therebetween.

Disposed in a needle lumen 164 formed in the shaft 100 is a needle 180 which connects to the control shaft 122 at the proximal end of shaft 100. Needle mechanism 180 slides between a retracted position in which it is housed in the lumen 164 near the distal end of the shaft 100 and an extended position in which it extends into the sliding tip 160 when the tip is in its closed position. As a result, if a valve leaflet has been captured between the tip 160 and the distal end of shaft 100 the needle may be extended from the lumen 164 by moving control shaft 122 to puncture the captured leaflet and pass completely through it.

The distal end of the shaft 100 also contains an artificial chorda, or suture 18 that is to be deployed in the patient's heart. The suture 18 is typically a 4-0 or 5-0 suture manufactured by a company such as Gore-Tex. This suture 18 is deployed by the operation of the grasping mechanism and the needle mechanism 180 as described in more detail below.

The shaft 100 has a size and shape suitable to be inserted into the patient's chest and through the left ventricle cardiac wall and form a water-tight seal with the heart muscle. It has a circular or ellipsoidal cross-section and it houses the control links between the handle end and the intracardiac end of the instrument as well as a fiber optic visualization system described in more detail below.

Figure 8B:
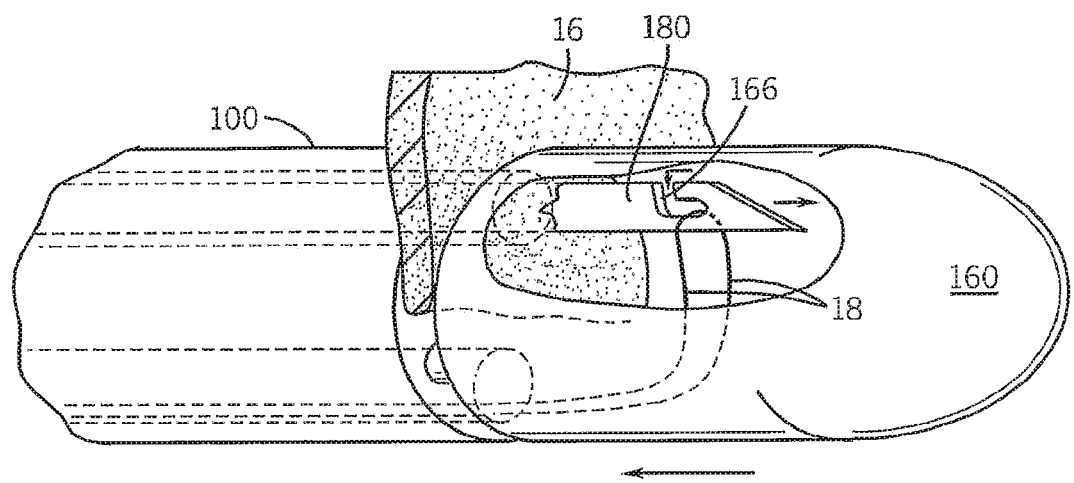
FIG. 8B is a detailed isometric view of the preferred embodiment of the suture deployment system showing the tip of the distal end of the instrument closing on the leaflet to grasp the leaflet such that the needle can puncture and push the suture through the leaflet.
Figure 8C:
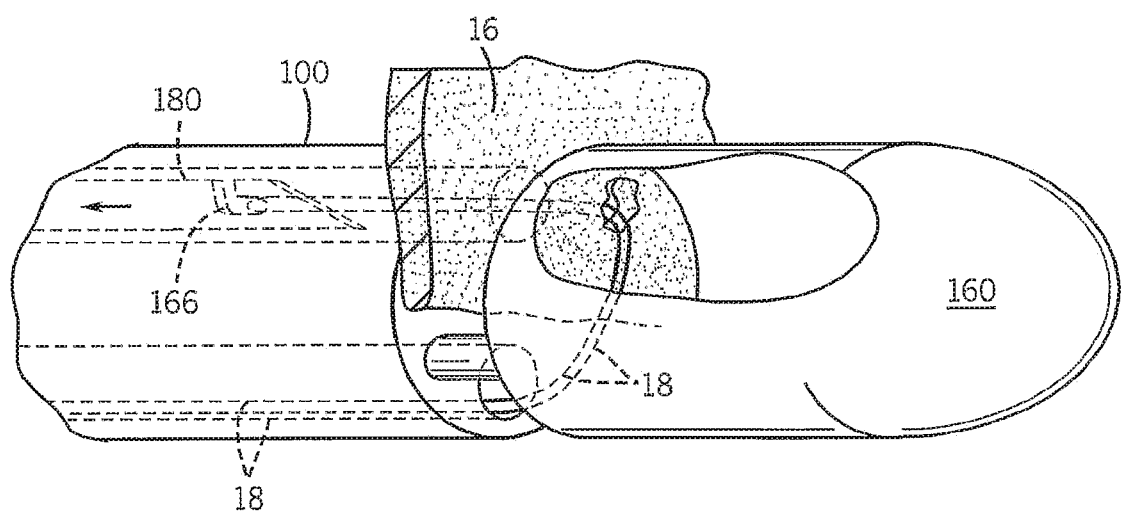
FIG. 8C is a detailed isometric view of the preferred embodiment of the suture deployment system showing the needle retracting back through the leaflet to pull the suture loop back through the puncture opening in the leaflet.
Figure 8D:
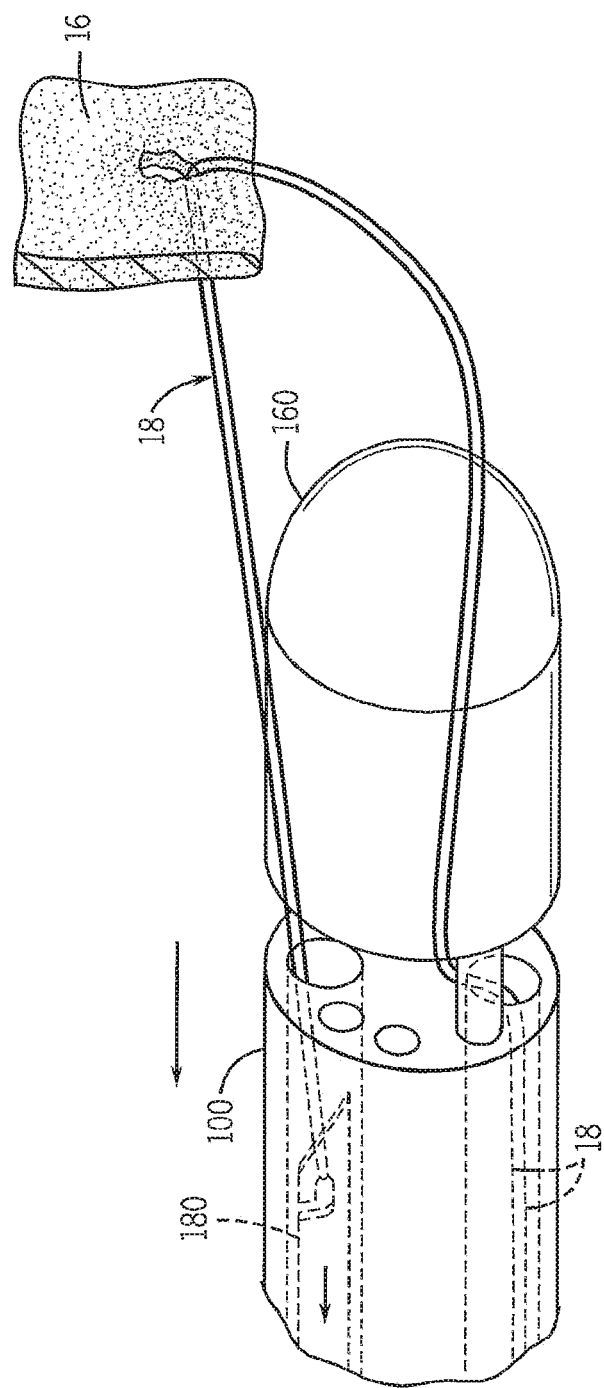
FIG. 8D is a detailed isometric view of the preferred embodiment of the suture deployment system showing the distal end of the instrument releasing the leaflet and pulling both ends and the midpoint of the suture as the instrument withdraws from the patient's heart.
Figure 8E:
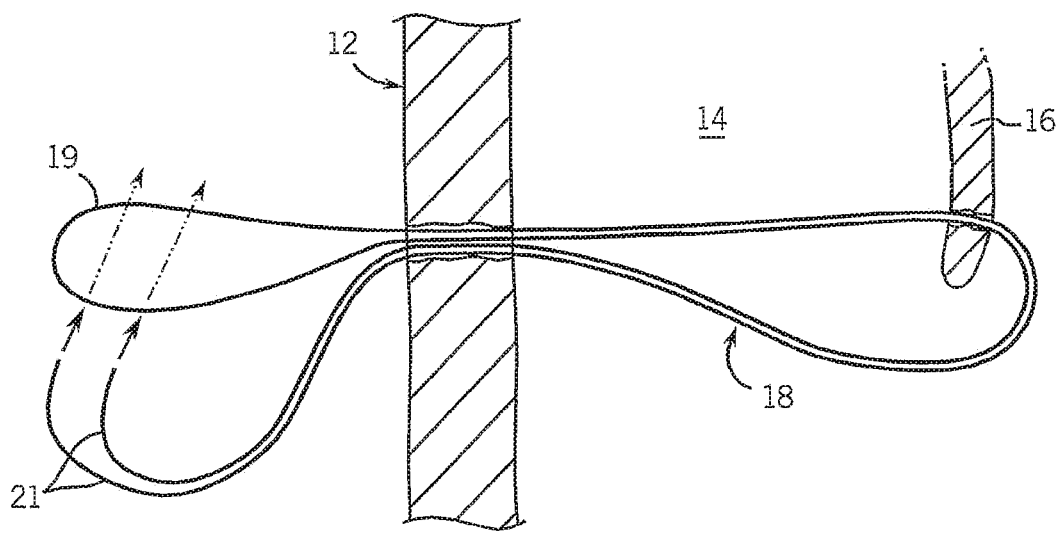
FIG. 8E is a detailed side elevation view of the preferred embodiment of the suture deployment where the suture is released from the instrument and the two suture ends are inserted through the loop.
Figure 8F:
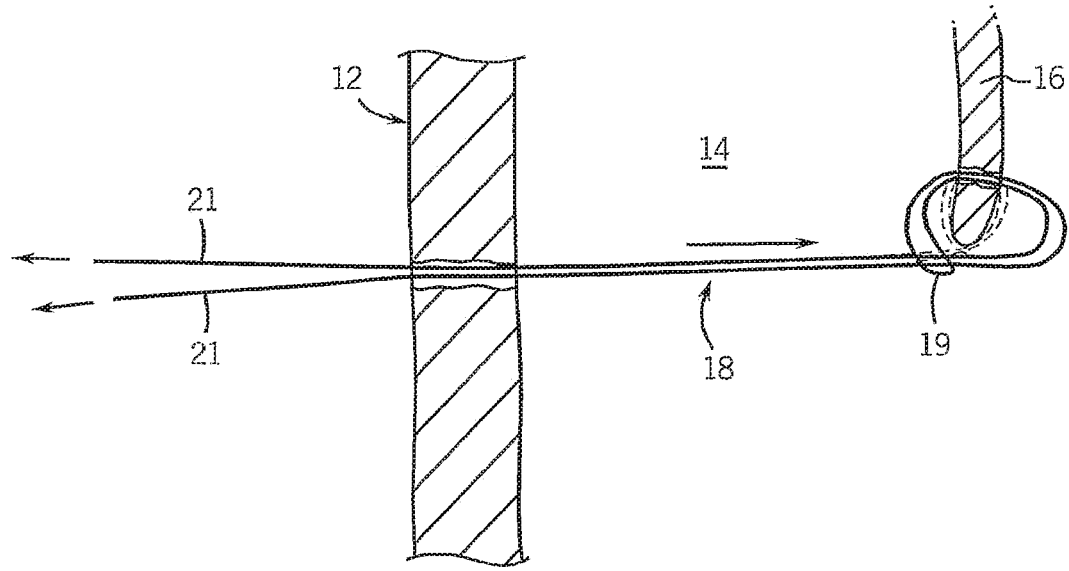
FIG. 8F is a detailed side elevation view of the preferred embodiment of the suture deployment system wherein the ends of the suture are pulled and the loop of the suture slides back along the suture to form a Larks head around the edge of the valve leaflet.

As shown in FIGS. 8A-8F, the preferred embodiment of the suture deployment system at the distal end of the instrument 10 is positioned around a valve leaflet 16 to be repaired as shown in FIG. 8A. The suture 18 is folded at the middle to form a loop 19 that is positioned in the tip 160. Both ends of the suture 18 are disposed in a suture lumen 165 formed in the shaft 100 beneath the rods 162. As shown in FIG. 8B, the valve leaflet 16 is grasped by closing the tip 160, and the needle 180 is extended to puncture the leaflet 16 and extend into the tip 160. A notch 166 formed on one side of the needle 180 hooks the suture loop 19. The needle 180 is then retracted back through the leaflet 16 to pull the suture loop 19 through the puncture opening as shown in FIG. 8C. The leaflet 16 is then released and the instrument 10 is withdrawn from the heart as shown in FIG. 8D pulling both ends and the midpoint of the suture 18 with it. As shown in FIG. 8E, the suture 18 is released by the instrument 10 and the surgeon inserts the two suture ends 21 through the loop 19 at its midpoint. The ends 21 are then pulled and the loop 19 slides along the suture 18 back into the heart chamber 14 where it forms a Larks head around the edge of the valve leaflet as shown in FIG. 8F.

Multiple sutures 18 may be implanted in this manner until a satisfactory result is obtained. After deployment of the sutures 18, the heart wall incision is repaired by either a pre-positioned purse-string suture or by any kind of appropriate hemostatic device or technique. Hemostasis is checked, appropriate chest drainage tubes are positioned and secured, and all incisions are closed.

Figure 9A:
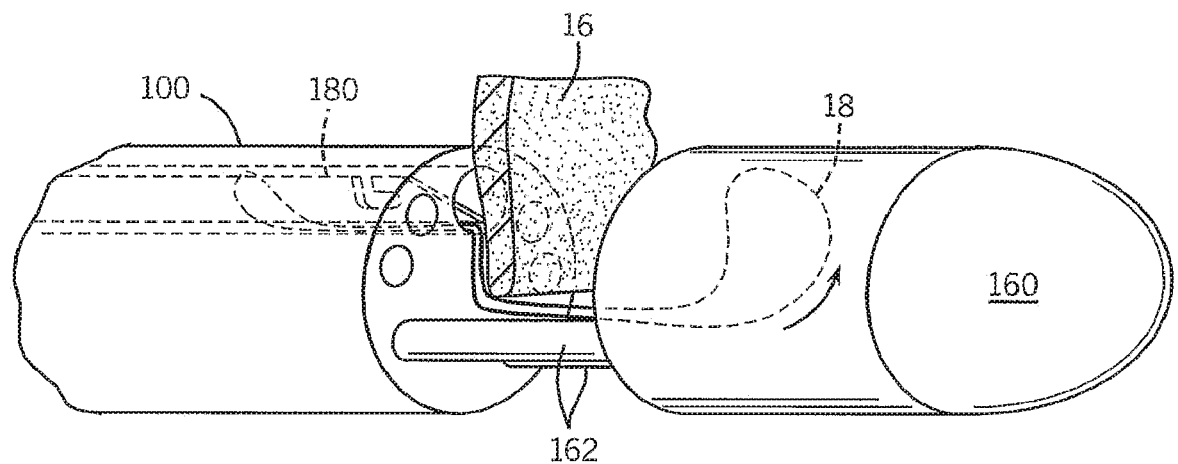
FIG. 9A is a detailed isometric view of a second embodiment of the suture deployment system showing the tip of the distal end of the instrument grasping the heart valve leaflet and showing a suture that is a closed loop with one end of the loop disposed in the tip of the instrument and the other end disposed in the lumen and wrapped around the needle.
Figure 9B:
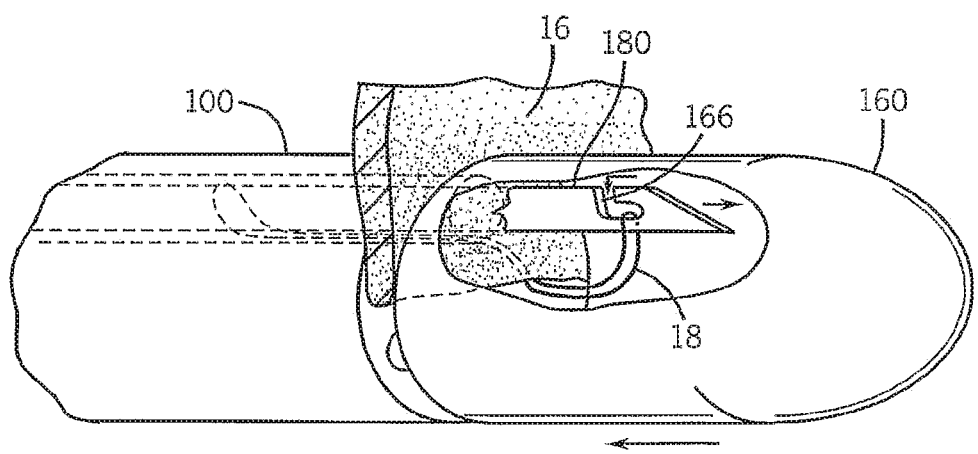
FIG. 9B is a detailed isometric view of a second embodiment of the suture deployment system showing the needle puncturing the leaflet and pushing the suture through the leaflet.
Figure 9C:
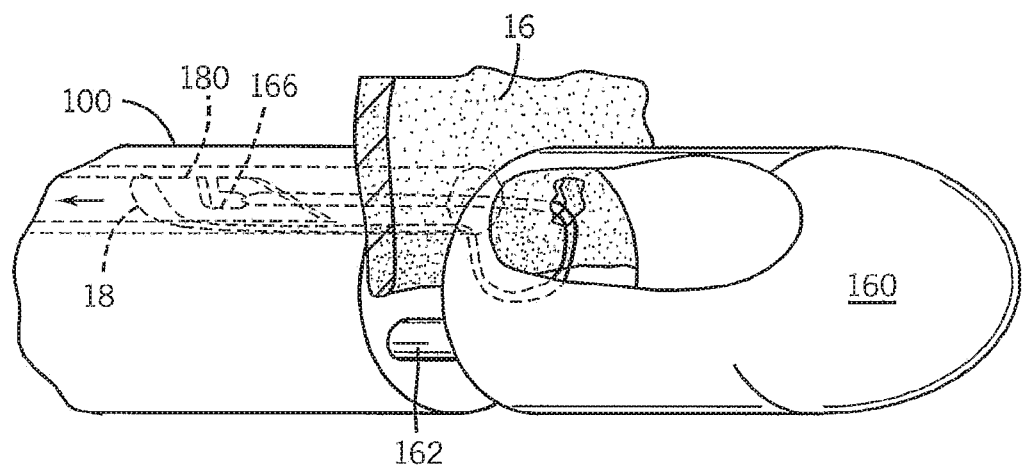
FIG. 9C is a detailed isometric view of a second embodiment of the suture deployment system showing the needle retracting back through the leaflet to pull the looped suture back through the opening in the leaflet and showing the instrument releasing the leaflet.
Figure 9D:
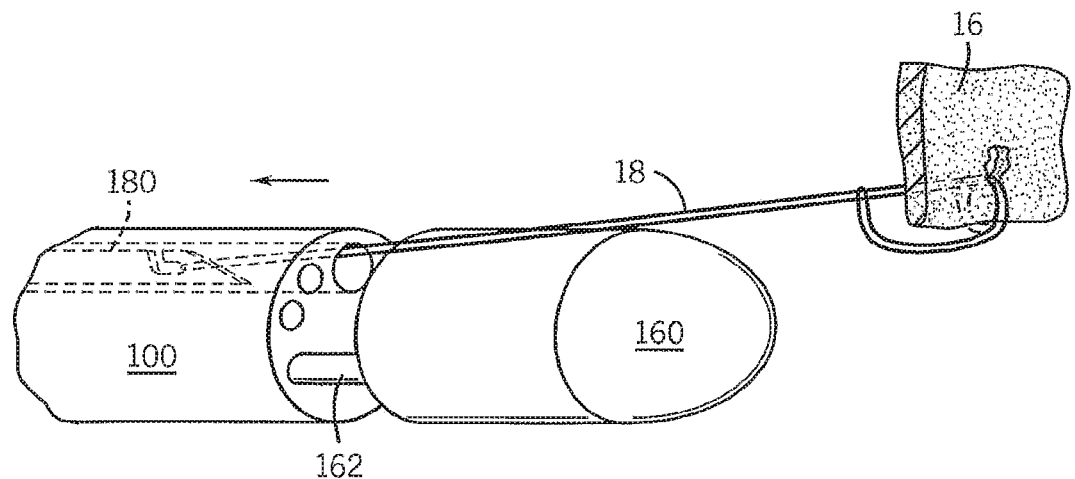
FIG. 9D is a detailed isometric view of a second embodiment of the suture deployment system showing the instrument withdrawing to slide the unhooked end of the suture along the length of the needle towards the leaflet to form a Larks head around the leaflet's edge.

As shown in FIGS. 9A-9D, a second embodiment of the suture deployment system at the distal end of the instrument 10 is positioned around a valve leaflet 16 to be repaired as shown in FIG. 9A. The suture 18 in this embodiment is a closed loop with one end of the loop disposed in the tip 160 and its other end disposed in the lumen 164 and wrapped around the needle 180. The needle 180 is extended through the grasped valve leaflet 16 into the instrument tip 160 where it hooks one end of the looped suture 18 in a notch 166 formed on one side of the needle as shown in FIG. 9B. The needle 180 is then retracted to pull the looped suture 18 through the puncture opening in the leaflet 16. The leaflet is then released as shown in FIG. 9C by sliding the tip 160 to its open position. The instrument 10 is then withdrawn as shown in FIG. 9D to slide the unhooked end of the looped suture 18 along the length of the needle toward the leaflet 16 where it forms a Larks head around the leaflet edge.

The instrument 10 is then withdrawing from the heart chamber 14 pulling the hooked end of the suture 18 through the heart wall. The suture 18 is secured to the outside of the heart apex.

Figure 10A:
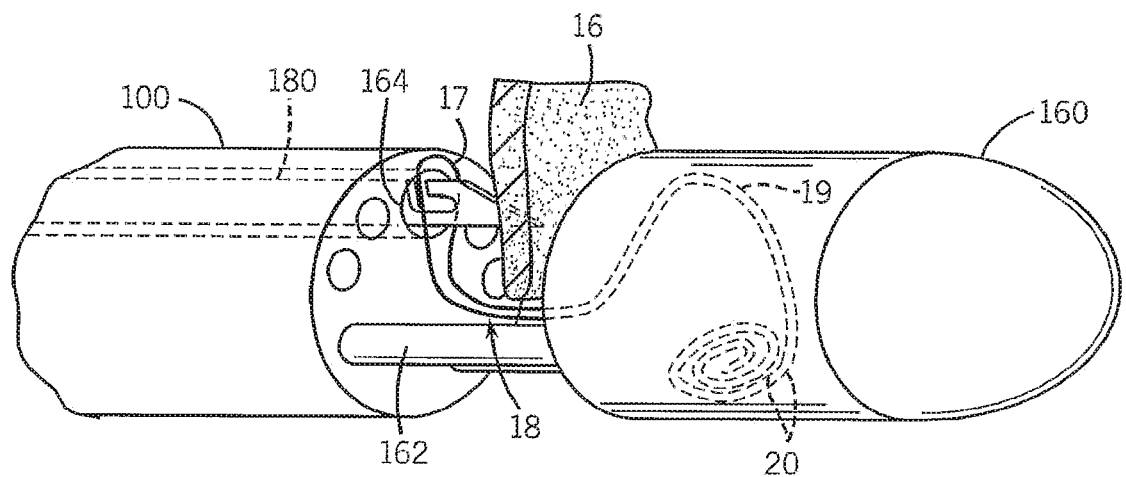
FIG. 10A is a detailed isometric view of a third embodiment of the suture deployment system showing the tip of the distal end of the instrument grasping the heart valve leaflet and showing the midpoint of the suture being looped around the lumen and the two loose ends of the suture being coiled up in the tip of the distal end of the instrument.
Figure 10B:
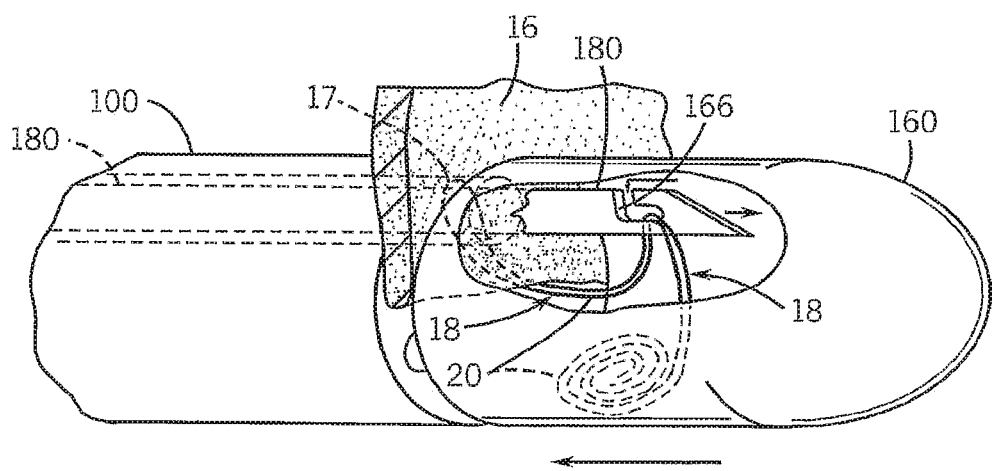
FIG. 10B is a detailed isometric view of a third embodiment of the suture deployment system showing the needle puncture and push the suture through the leaflet and through the loop of the free ends of the suture wherein the needle then hooks the free ends of the suture.
Figure 10C:
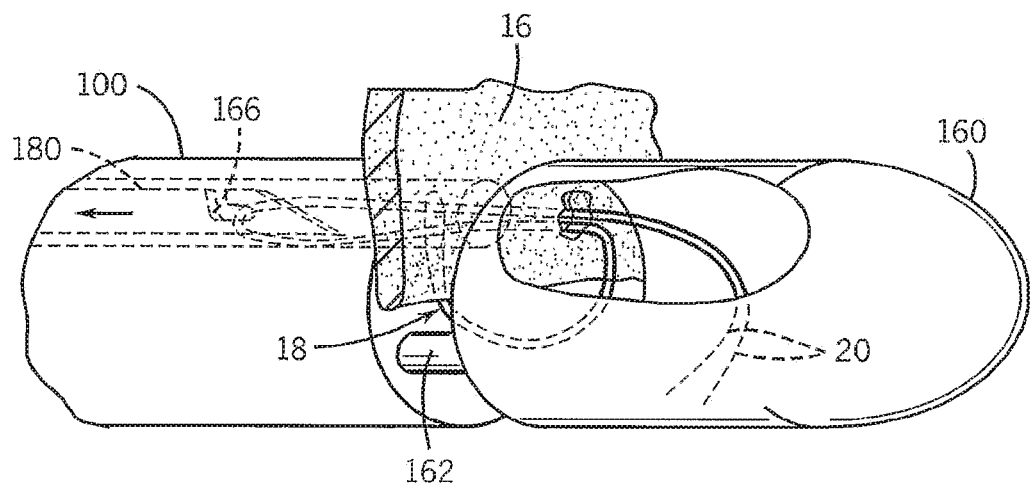
FIG. 10C is a detailed isometric view of a third embodiment of the suture deployment system showing the needle retracting back through the leaflet and showing the instrument releasing the leaflet.
Figure 10D:
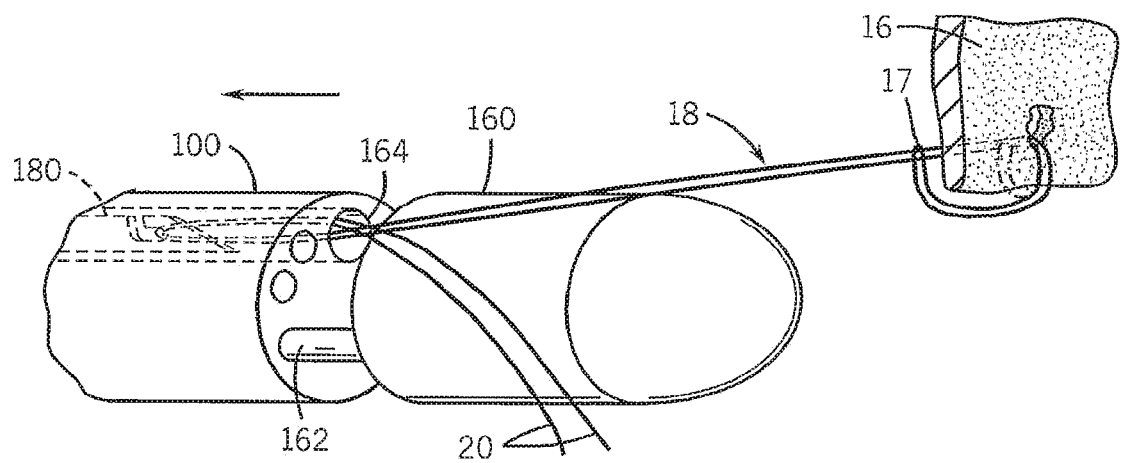
FIG. 10D is a detailed isometric view of a third embodiment of the suture deployment system showing the instrument withdrawing from the heart to pull the free ends of the suture back through the valve leaflet and forming a Larks head around the leaflet's edge by the midpoint of the suture.

As shown in FIGS. 10A-10D, a third embodiment of the suture deployment system at the distal end of the instrument 10 is positioned around a valve leaflet 16 to be repaired as shown in FIG. 10A. The midpoint 17 of the suture 18 is looped around the lumen 164 and its two loose ends 20 are coiled up in the tip 160. After the tip 160 is closed to capture the valve leaflet 16, the needle 180 is extended through the grasped valve leaflet 16 into the instrument tip 160. The free ends 20 of the suture 18 are positioned in the tip 160 to form a loop 19 and a notch 166 formed on one side of the needle extends through this loop 19 and "hooks" the free ends of the suture 18 as shown in FIG. 10B. The needle 180 is then retracted back into the lumen 164 to pull the hooked ends of the suture 18 through the puncture opening in the leaflet 16. The leaflet is then released as shown in FIG. 10C by sliding the tip 160 to its open position. The instrument 10 is then withdrawn from the heart as shown in FIG. 10D to pull the free ends 20 back through the valve leaflet 16 and a Larks head is formed around the leaflet edge by the midpoint 17 of the suture 18.

The instrument 10 is then withdrawn from the heart chamber 14 pulling the free ends 20 of the suture 18 through the heart wall. The free ends 20 of the suture 18 are secured to the outside of the heart apex.

Other suture deployment systems are possible where, for example, the needle may penetrate through the leaflet and link up with a snap fitting device that is attached to one end of the looped suture 18 in the instrument tip 160. The needle then withdraws pulling the device and looped suture back through the penetration opening in the leaflet as described above.

As shown in FIG. 7 to enhance visibility during this procedure, four fiberoptic channels 170 extend along the length of the instrument shaft 100 and terminate at its distal end. Each channel 170 contains at least one illuminating fiber which connects at its extrathoracic end to a white light source (not shown in the drawings). Each channel 170 also contains at least one sensor fiber which conveys reflected light from the distal end back to a visualization monitor (not shown in the drawings) connected to its extrathoracic end. In the preferred embodiment each channel 170 includes two illuminating fibers and two sensor fibers.

The four fiberoptic channels 170 are disposed around the needle lumen 164 such that when a valve leaflet 16 is properly grasped, the valve leaflet tissue 16 rests against the distal end of all the fibers 170. As a result, light is reflected off the tissue back into the sensor fibers and four white circles are displayed on the visualization monitor. When the leaflet 16 is not properly pressed against the distal end of a channel 170, light is not reflected from the leaflet 16 and the visualization monitor displays the red color reflected from blood. When no valve tissue is captured, the monitor shows four red dots and when valve tissue is captured, the dots corresponding to the fiberoptic channels 170 contacting the tissue turn white. If the monitor shows all four dots as white, it means that the valve tissue capture is optimal. If only the upper two dots turn white and the bottom dots remain red, the "bite" on the valve leaflet 16 is too shallow for a proper attachment of the suture 18.

In addition to the fiberoptic visualization system that insures that a valve leaflet is properly captured, other real-time visualization systems are employed to help guide the instrument 10 to the valve leaflet 16. Preferably a transesophageal or intravascular color-Doppler echocardiography system is used for this purpose. As explained above, this imaging system is also used to determine the length of the neo-implanted artificial chordae in real-time by observing reduction or disappearance of regurgitation by transesophageal or intravascular color-Doppler echocardiography.

What is claimed is:

1. A method of repairing a heart valve in a beating heart of a patient with a suture, the suture including a loop portion and a pair of free ends, the method comprising:
   positioning the loop portion of the suture adjacent a first side of a moving heart valve leaflet;
   drawing the loop portion of the suture through the leaflet to a second side of the leaflet;
   inserting the pair of free ends of the suture through the loop portion; and
   tightening the suture to form a knot around an edge of the leaflet,
   wherein the step of inserting the pair of free ends of the suture through the loop portion is done exterior to the heart.

2. The method of claim 1, wherein the knot is a Lark's Head knot.

3. The method of claim 1, further comprising anchoring the pair of free ends of the suture to a location within the heart.

4. The method of claim 3, wherein the location in the heart is a papillary muscle.

5. The method of claim 1, further comprising extending the suture over the edge of the leaflet.

6. The method of claim 1, further comprising:
   inserting a heart valve repair device into the heart and the step of positioning the loop portion of the suture adjacent the first side of the moving heart valve leaflet is done with the heart valve repair device.

7. The method of claim 6, wherein the step of drawing the loop portion of the suture through the leaflet to a second side of the leaflet is done by extending a needle of the heart valve repair device from the second side of the leaflet to the first side of the leaflet to retrieve the suture by retracting the needle back to the second side of the leaflet.

8. The method of claim 7, wherein the needle retrieves the suture by hooking the loop portion in a notch of the needle.

9. The method of claim 7, further comprising withdrawing the heart valve repair device from the heart and then the step of inserting the pair of free ends of the suture through the loop portion is done exterior to the heart.

10. The method of claim 1, wherein the step of inserting the pair of free ends of the suture through the loop portion includes inserting the pair of free ends through the loop portion at a midpoint of the suture.

11. The method of claim 1, wherein the first side of the leaflet is a superior surface of the leaflet and the second side of the leaflet is an inferior surface of the leaflet.

12. A method of repairing a heart valve in a beating heart of a patient with a suture, the method comprising:

inserting a heart valve repair device into the heart;

grasping a moving heart valve leaflet with the heart valve repair device;

inserting a suture through the leaflet with the heart valve repair device; and forming a Larks head knot with the suture around an edge of the leaflet, including inserting a pair of free ends of the suture through a loop portion of the suture and tightening the suture with the pair of free ends of the suture inserted through the loop portion of the suture to form the Lark's Head knot around the edge of the leaflet, and further comprising withdrawing the heart valve repair device from the heart and the step of inserting the pair of free ends of the suture through the loop portion is done exterior to the heart.

13. The method of claim 12, further comprising:

positioning a loop portion of the suture adjacent a first side of the leaflet with the heart valve repair device; and wherein the step of inserting the suture through the leaflet includes drawing the loop portion of the suture through the leaflet to a second side of the leaflet.

14. The method of claim 13, wherein the step of drawing the loop portion of the suture through the leaflet includes extending a needle of the heart valve repair device from the second side of the leaflet to the first side of the leaflet to retrieve the suture by retracting the needle back to the second side of the leaflet.

15. The method of claim 14, wherein the needle retrieves the suture by hooking the loop portion in a notch of the needle.

16. The method of claim 12, wherein the step of inserting the pair of free ends of the suture through the loop portion includes inserting the pair of free ends through the loop portion at a midpoint of the suture.

17. The method of claim 12, further comprising extending the suture over the edge of the leaflet.

18. The method of claim 12, further comprising anchoring the suture to a location within the heart.

19. The method of claim 18, wherein the location in the heart is a papillary muscle.

* * * * *